United States Patent
Porro et al.

(10) Patent No.: US 10,429,335 B2
(45) Date of Patent: Oct. 1, 2019

(54) INTEGRATED GAS SENSOR DEVICE, IN PARTICULAR FOR DETECTING CARBON MONOXIDE (CO)

(71) Applicant: STMICROELECTRONICS S.R.L., Agrate Brianza (IT)

(72) Inventors: Fabrizio Porro, Portici (IT); Valeria Casuscelli, Naples (IT); Francesco Foncellino, Caserta (IT); Giovanna Salzillo, Teverola (IT); Luigi Giuseppe Occhipinti, Ragusa (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 0 days.

(21) Appl. No.: 15/658,171

(22) Filed: Jul. 24, 2017

(65) Prior Publication Data

US 2017/0322170 A1   Nov. 9, 2017

Related U.S. Application Data

(62) Division of application No. 14/318,321, filed on Jun. 27, 2014, now Pat. No. 9,746,439.

(30) Foreign Application Priority Data

Jun. 28, 2013   (IT) .............................. MI2013A1096

(51) Int. Cl.
  *G01N 27/26*   (2006.01)
  *G01N 7/00*   (2006.01)
  (Continued)

(52) U.S. Cl.
  CPC ......... *G01N 27/26* (2013.01); *G01N 27/4045* (2013.01); *G01N 33/0027* (2013.01)

(58) Field of Classification Search
  CPC .......... G01N 27/26; G01N 7/00; G01N 21/00; G01N 27/00; G01N 31/00; G01N 33/00
  (Continued)

(56) References Cited

U.S. PATENT DOCUMENTS

| 4,076,596 A | 2/1978 | Connery et al. |
| 4,812,221 A | 3/1989 | Madou et al. |

(Continued)

FOREIGN PATENT DOCUMENTS

WO   93/23745 A1   11/1993

OTHER PUBLICATIONS

Maseeh, F. et al. "A Novel Silicon Micro Amperometric Gas Sensor", 1991 IEEE, pp. 359-362.

(Continued)

*Primary Examiner* — Brian J. Sines
(74) *Attorney, Agent, or Firm* — Seed IP Law Group LLP

(57) ABSTRACT

It is described an integrated gas sensor device comprising a silicon substrate and an oxide layer on the silicon substrate, as well as a working electrode, a counter electrode and a reference electrode, on the oxide layer, the working electrode and the counter electrode having respective active area exposed to an environmental air through at least a plurality of first openings and a plurality of second openings in the oxide layer in correspondence of the working electrode and of the counter electrode, further comprising an electrolyte layer portion and a hydrogel layer portion on the electrolyte layer portion, the electrolyte and hydrogel layer portions having a same size, suitable to cover at least the working, counter and reference electrodes, the hydrogel layer portion acting as a "quasi solid state" water reservoir.

20 Claims, 6 Drawing Sheets

(51) Int. Cl.
  *G01N 21/00* (2006.01)
  *G01N 27/00* (2006.01)
  *G01N 31/00* (2006.01)
  *G01N 33/00* (2006.01)
  *G01N 27/404* (2006.01)

(58) Field of Classification Search
  USPC ............... 29/592, 592.1; 438/48, 49; 422/83
  See application file for complete search history.

(56) References Cited

U.S. PATENT DOCUMENTS

| | | |
|---|---|---|
| 5,036,704 A | 8/1991 | Pusatcioglu et al. |
| 5,215,643 A | 6/1993 | Kusanagi et al. |
| 5,331,310 A | 7/1994 | Stetter et al. |
| 6,180,288 B1 | 1/2001 | Everhart et al. |
| 6,682,638 B1 | 1/2004 | Prohaska et al. |
| 6,695,959 B2 | 2/2004 | Kiesele |
| 6,915,678 B2 | 7/2005 | Fleischer et al. |
| 2004/0074785 A1 | 4/2004 | Holker et al. |
| 2006/0015083 A1* | 1/2006 | Munro ............... A61L 15/425 604/367 |
| 2006/0035561 A1* | 2/2006 | Heo ............... H01J 9/025 445/50 |
| 2009/0301876 A1 | 12/2009 | Wagner et al. |
| 2014/0012114 A1* | 1/2014 | Zevenbergen ..... A61B 5/14521 600/346 |

OTHER PUBLICATIONS

P.D. van der Wal et al., "The development of a Nafion based amperometric carbon monoxide sensor for domestic safety", Analusis, 1999, 27 N° 4, EDP Sciences, Wiley-VCH 1999, p. 347-351.

* cited by examiner

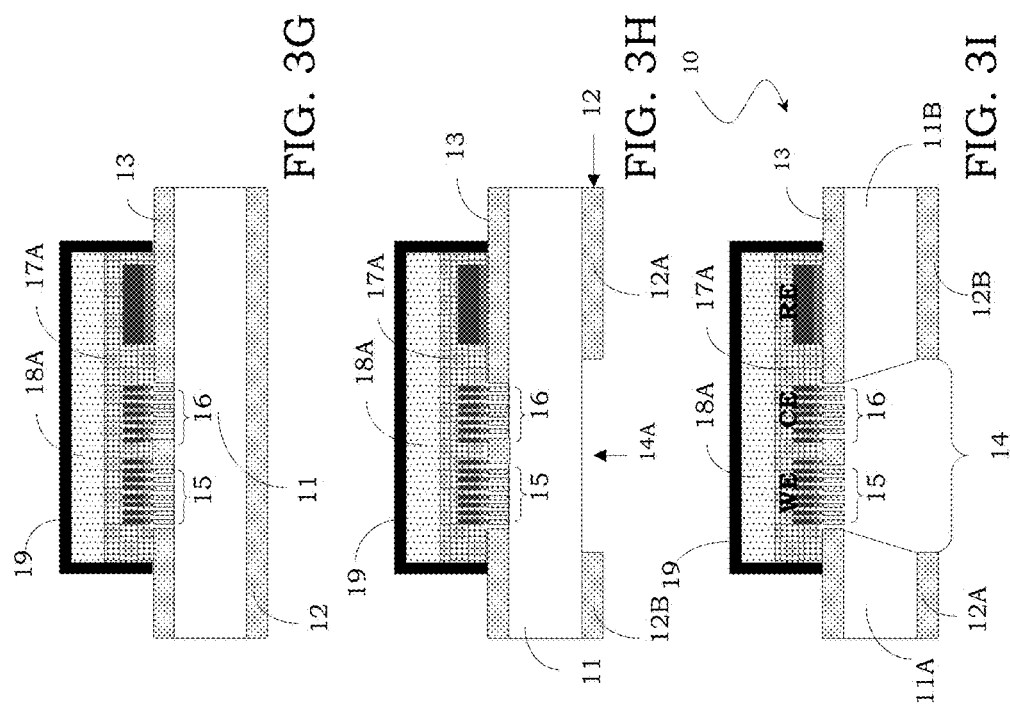

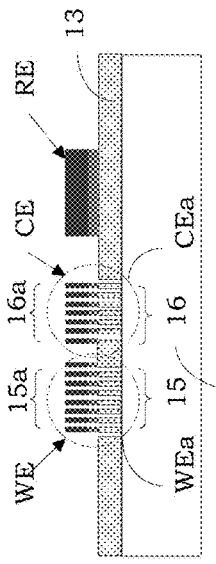
FIG. 5D
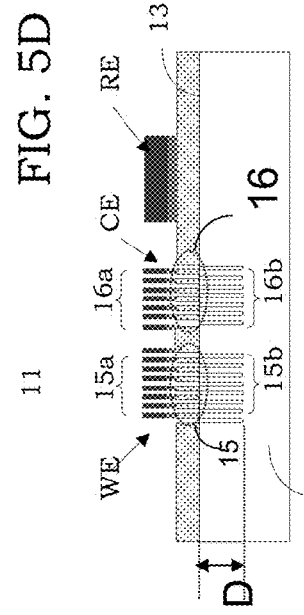
FIG. 5E
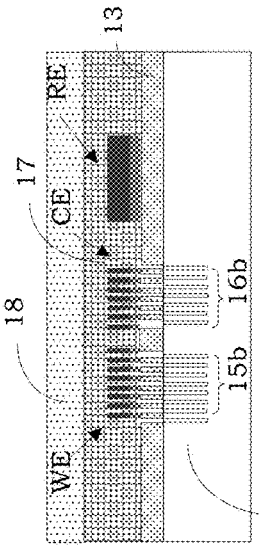
FIG. 5F
FIG. 5A
FIG. 5B
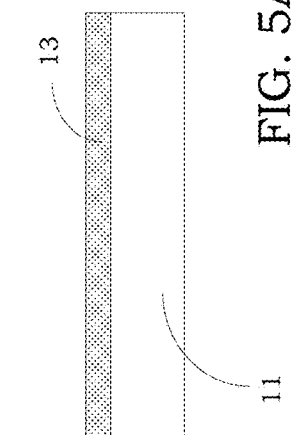
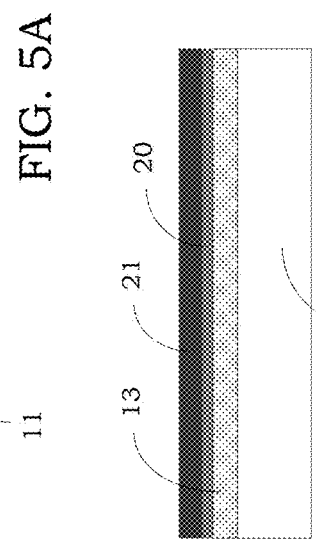
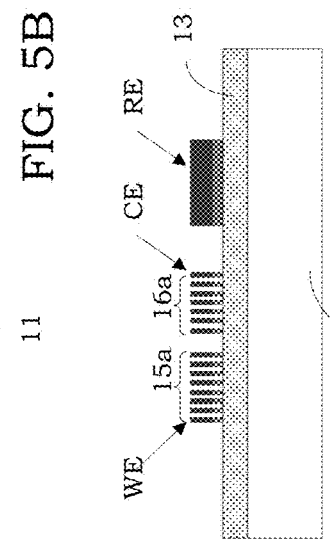
FIG. 5C

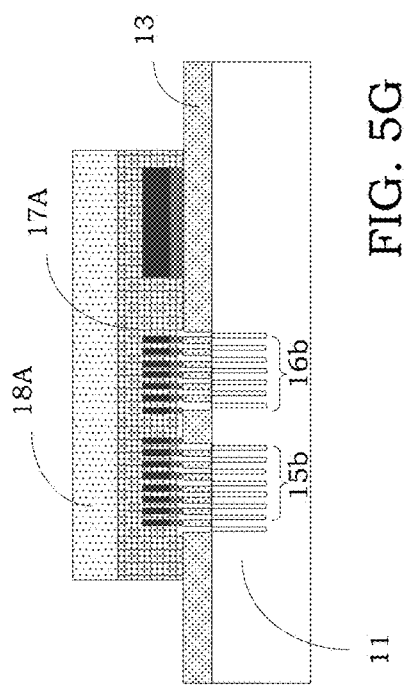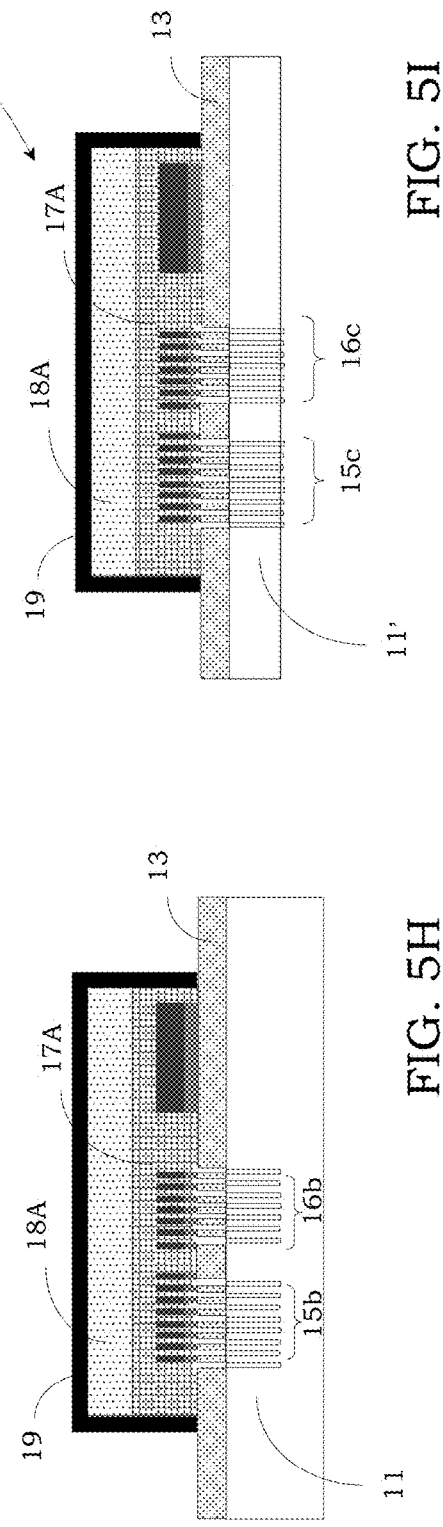

INTEGRATED GAS SENSOR DEVICE, IN PARTICULAR FOR DETECTING CARBON MONOXIDE (CO)

BACKGROUND

Technical Field

The present disclosure relates to an integrated gas sensor device. The disclosure also relates to a manufacturing process of an integrated gas sensor device.

Description of the Related Art

As it is well known, a gas sensor is a device which detects the presence of various gases within an area, usually as part of a safety system. This type of equipment is used to detect a gas leak and interfaces with a control system so that a process can be automatically shut down. A gas sensor can also sound an alarm to operators in the area where the leak is occurring, giving them the opportunity to leave the area. This type of device is important because there are many gases that can be harmful to organic life, such as humans or animals.

In this field, a carbon monoxide sensor or CO sensor is a device that detects the presence of the carbon monoxide (CO) gas in order to prevent carbon monoxide poisoning. In fact, it is known that CO attaches to the hemoglobin (in the blood stream) with an affinity 200× stronger than oxygen, producing inadequate amounts of oxygen travelling through the body, with symptoms like headache, fatigue, nausea, and dizziness that could resemble many common illnesses, and thus being misdiagnosed and mistreated.

Elevated levels of CO can be thus dangerous to humans depending on the amount present and length of exposure. In particular, also small concentrations of CO can be harmful over longer periods of time while increasing concentrations are dangerous even in case of reduced exposure times.

The CO sensors are particularly important due to the fact that CO is colorless, tasteless and odorless (unlike smoke from a fire), and thus detection in a home environment is impossible without a suitable warning device.

At present carbon monoxide sensing devices are readily available for many industrial applications. The sensors used in these devices include electrochemical sensors, semiconductor sensors, colorimetric detectors and infrared detectors.

In the field of electrochemical sensors, the amperometric sensors are largely used to detect a wide range of electro-active gases, for instance carbon monoxide.

Amperometric gas sensors usually comprise three electrodes: a working electrode, a counter electrode and a reference electrode. These electrodes are placed in contact with an electrolytic medium, such as an electrolyte solution, or a polymer electrolyte. A potential is then applied to the working electrode in order to induce an electrochemical reaction of the sensed gas which generates a current, proportional to the gas concentration.

By selecting proper metal electrodes, electrolytes and working potentials, this same device structure may be made optimized for detection of different gaseous analytes (e.g., NOx; O2, CO2 . . . ).

The gas has to diffuse from the environment through a diffusion barrier and then reaches the working electrode surface. The working electrode is a so called gas diffusion electrode.

As for CO sensors, the electrochemical detection of carbon monoxide is based on the reaction of the same at the working electrode, usually made of platinum, which is able to oxidize carbon monoxide. Essentially, carbon monoxide is oxidized at the platinum working electrode to carbon dioxide while oxygen is consumed at the counter electrode. As previously indicated, the current that is generated is a measure for the amount of carbon monoxide.

Because of the chemical reaction of CO, the working and counter electrodes do not maintain a constant potential. Therefore a separate reference electrode is also necessary. All three electrodes are gas diffusion electrodes.

In particular, the working and counter electrodes are in contact with an external environment, and thus with the environmental air, via a gas diffusion barrier. The reference electrode is shielded from carbon monoxide and is kept in a constant environment and therefore maintains a constant potential. For the counter reaction, sufficient supply of oxygen is also important.

In case of a carbon monoxide detection, the electrochemical sensors have advantages over sensors obtained by other technologies in that they have a highly accurate and linear output to carbon monoxide concentration, utilize minimal power since operating at room temperature, and have a long lifetime. Main drawbacks of this kind of sensors are high prices and the need for frequent recalibration of the same.

Other problems are encountered when the gas sensors are to be miniaturized, the final price of the miniaturized sensor devices being even higher.

Known gas sensors are described for instance in the article to Maseeh et al. entitled "A Novel Silicon Micro Amperometric Gas Sensor", IEEE, 1991, 91CH2817-5 and in the article to P. D. van del Wal et al. entitled: "The development of a Nafion based amperometric carbon monoxide sensor for domestic safety", Analusis, 1999, 27, No. 4, EDP Sciences, Wiley-VCH.

BRIEF SUMMARY

The present disclosure relates to an integrated gas sensor device comprising an oxide layer on a substrate, as well as a working electrode, a counter electrode and a reference electrode, on the oxide layer, the working electrode and the counter electrode having respective active areas exposed to an environmental air through at least a plurality of first openings and a plurality of second openings in the oxide layer in correspondence of the working electrode and of the counter electrode.

The disclosure particularly, but not exclusively, relates to an integrated gas sensor device for detecting carbon monoxide (CO) and the following description is made with reference to this field of application for convenience of explanation only.

One or more embodiments of the present disclosure overcomes the several problems identified above affecting the known gas sensor devices.

One or more embodiments of the present disclosure provide an integrated gas sensor device, in particular for detecting carbon monoxide (CO), having structural and functional characteristics which allow to improve the overall sensing properties and to allow its miniaturizing by using well known, stable and low cost integration processes, in this way overcoming the limits which still affect the devices realized according to the prior art.

In one embodiment the integrated gas sensor device includes a hydrogel layer portion covering an electrolyte layer portion in order to act as a "quasi solid state" water reservoir. The integrated gas sensor device may include a silicon substrate and an oxide layer on the silicon substrate, as well as a working electrode, a counter electrode and a reference electrode, on said oxide layer, said working electrode and counter electrode having respective active area exposed to an environmental air through at least a plurality of first openings and a plurality of second openings in said oxide layer in correspondence of said working electrode and of said counter electrode, characterized in that it further comprises an electrolyte layer portion and a hydrogel layer portion on said electrolyte layer portion, said electrolyte and hydrogel layer portions having a same size, suitable to cover at least said working, counter and reference electrodes, said hydrogel layer portion acting as a "quasi solid state" water reservoir.

Other embodiments of the gas sensor devices according to the present disclosure may comprise the following supplemental and optional features, taken alone or in combination.

The active areas of the working and counter electrodes may have grid shapes comprising respective pluralities of third and fourth openings.

In particular, the active areas of the working and counter electrodes may have hexagonal grid shapes.

According to a further aspect of the disclosure, the electrolyte layer portion may fill in the third openings of the working electrode and the fourth openings of the counter electrode.

The electrolyte layer portion may have a promoted adhesion on the oxide layer.

Moreover, the first and second openings and the third and fourth openings may be positioned in an aligned way, so that each of the first openings in the oxide layer follows a corresponding opening of the third openings and each of the second openings in the oxide layer follows a corresponding opening of the fourth openings.

The first and second openings may have the same size and shape than the third and fourth openings. Alternatively, the first and second openings may have smaller size and shape than the third and fourth openings.

Moreover, the working, counter and reference electrodes may be formed by at least a first metal and a second metal, superimposed each other.

According to this aspect of the disclosure, the first metal may be titanium and may be covered by the second metal which may be platinum.

According to another aspect of the disclosure, the integrated gas sensor device may further comprises a main opening provided in the silicon substrate so as to reach the oxide layer and the first and second openings of the oxide layer, so exposing the active areas of the working and counter electrodes, respectively, to the environmental air.

In particular, the main opening may be tapered and may have a transversal dimension which reduces starting from the silicon substrate to the oxide layer.

According to another aspect of the disclosure, the integrated gas sensor device may further comprise a plurality of trench-like openings realized in the substrate in correspondence with the first and second openings realized in the oxide layer.

More particularly, the trench-like openings of the silicon substrate may have the same size and shape than the first and second openings of the oxide layer.

The integrated gas sensor device may further comprise a capping layer, covering the electrolyte layer portion and the hydrogel layer portion and in contact with the same and also with the second oxide layer. The capping layer may be shaped as an inverse U, or another shape suitable to obtain a closed volume containing the electrolyte layer portion and the hydrogel layer portion.

According to an aspect of the disclosure, the electrolyte layer portion may comprise an aqueous system of acids, bases and salts, a polymer electrolyte, a non aqueous system like propylene carbonate, lithium perchlorate, polyethylene oxide lithium chloride, ionic liquids.

In particular, the electrolyte layer portion may be made of Nafion®, a sulfonated tetrafluoroethylene based fluoropolymer-copolymer produced by DuPont.

According to another aspect of the disclosure, the hydrogel layer portion may comprise an electrolytic hydrogel, that combines the electrolyte layer portion and hydrogel layer portion in a single layer having the functionalities of both electrolyte and hydrogel layers.

In particular, the electrolytic hydrogel may be chosen between 2-Hydroxyethylmethacrylate (HEMA) and ethylene glycol dimethacrylate (EGDM), polyvinyl alcohol (PVA), polyethylene glycol diacrylate (PEG-DA).

According to another aspect of the disclosure, the oxide layer may be a silicon oxide layer.

In addition, according to the present disclosure, there is provided a manufacturing process of an integrated gas sensor device comprising the steps of:

deposition of an oxide layer on a silicon substrate;

deposition of a first metal layer on the second oxide layer and of a second metal layer on the first metal layer;

patterning the first metal layer and the second metal layer to define a reference electrode, a working electrode and a counter electrode of the integrated gas sensor device, all simultaneously, the patterning step also defining respective openings of the working and counter electrodes;

etching the oxide layer and defining respective further openings in the second oxide layer, in correspondence with the openings of the working and counter electrodes, forming respective active areas of the working and counter electrodes with a grid like shape;

deposition of an electrolyte layer on the oxide layer;

deposition of a hydrogel layer on the electrolyte layer;

etching the electrolyte layer and hydrogel layer to obtain an electrolyte layer portion and a hydrogel layer portion having a same size, suitable to cover at least the working, counter and reference electrodes, the hydrogel layer portion acting as a "quasi solid state" water reservoir of the integrated gas sensor device; and exposing the active areas of the working and counter electrodes to an environmental air.

According to a further aspect of the disclosure, the step of etching the oxide layer may comprise a photolithographic process which uses a lithography mask for defining the further openings in the oxide layer having a smaller size and shape than the openings of the working and counter electrodes.

Alternatively, the step of etching the oxide layer may use the first and second metal layers, already patterned, as a hard mask combined with a further mask in order to define the further openings in the oxide layer having the same size and shape than the openings of the working and counter electrodes.

According to an aspect of the disclosure, the deposition step of the electrolyte layer may fill in the openings of the working and counter electrodes, thus completing the active areas of the working and counter electrodes, respectively.

Moreover, the patterning step of the first metal layer and the second metal layer may define openings having an hexagonal shape.

According to an aspect of the disclosure, the deposition step of an electrolyte layer may comprise a spin coating step.

In particular, the deposition step of an electrolyte layer may be followed by an annealing step at a temperature of 140° C. and by a socking step in sulfuric acid at a temperature of 90° C. and with a concentration of 0.5M.

The manufacturing process may comprise a step of surface treatment with alkane silanes of the oxide layer being performed before the deposition step of the electrolyte layer.

According to another aspect of the disclosure, the deposition step of a hydrogel layer may comprise a spin coating step.

In particular, the deposition step of a hydrogel layer is followed by a soaking step in water at a temperature of 90° C.

Moreover, according to an aspect of the disclosure, the deposition step of the first metal layer and second metal layer may deposit a first metal layer of titanium having a thickness between 5 and 30 nm, preferably equal to 20 nm and a second metal layer of platinum having a thickness between 80 and 120 nm, preferably equal to 100 nm.

The manufacturing process may further comprise a deposition step of a capping layer, covering the electrolyte layer portion and the hydrogel layer portion.

According to another aspect of the disclosure, the step of exposing the active areas of the working and counter electrodes to the environmental air comprises a step of:

deep back etching the silicon substrate to define an opening in the silicon substrate reaching the oxide layer and the further openings in correspondence with the working and counter electrodes.

Furthermore, according to another aspect of the disclosure, the deep back etching step of the silicon substrate uses micromachining techniques.

According to a further aspect of the disclosure, the manufacturing process may further comprises, before the step of exposing the active areas of the working and counter electrodes to the environmental air, a step of further etching the silicon substrate and realizing deep trenches in correspondence with the openings of said working and counter electrodes.

More particularly, the step of exposing the active areas of the working and counter electrodes to the environmental air comprises the step of:

back grinding the substrate to remove part thereof from an opposite side than the oxide layer until the deep trenches are fully opened to the environmental air, so as to form trench-like openings which form, with the openings of the oxide layer and the further openings of said working and counter electrodes a path for a gas flow to the active areas of the working and counter electrodes.

Finally, the step of realizing the deep trenches in the substrate comprises a deep reactive ion etching step which uses a same lithographic mask as the one used to obtain the openings in the oxide layer, so obtaining deep trenches having the same size and shape than the further openings of the working and counter electrodes.

The characteristics and advantages of the integrated gas sensor device and the corresponding manufacturing process according to the disclosure will be apparent from the following description of an embodiment thereof given by way of indicative and non limiting example with reference to the annexed drawings.

BRIEF DESCRIPTION OF THE SEVERAL VIEWS OF THE DRAWINGS

In the drawings:

FIGS. 3A-3I schematically show the integrated gas sensor device of FIG. 1 in different steps of its manufacturing process;

FIGS. 5A-5I schematically show the alternative embodiment of FIG. 4 in different steps of its manufacturing process.

DETAILED DESCRIPTION

Figure 1:
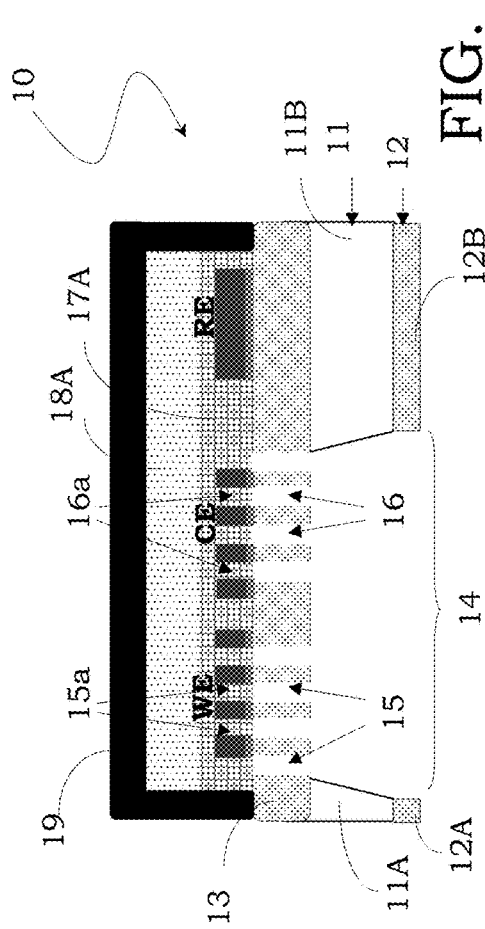
FIG. 1 schematically shows a side view of an integrated gas sensor device realized according to an embodiment of the disclosure.

With reference to the drawings, and in particular to FIG. 1, an integrated gas sensor device is globally and schematically indicated with 10.

In the following description, numerous specific details are given to provide a thorough understanding of embodiments. The embodiments can be practiced without one or more of the specific details, or with other methods, components, materials, etc. In other instances, well-known structures, materials, or operations, are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" "according to an embodiment" or "in an embodiment" and similar phrases in various places throughout this specification are not necessarily all referring to the same embodiment. Furthermore, the particular features, structures, or characteristics may be combined in any suitable manner in one or more embodiments.

As will be clarified by the following description, according to an embodiment of the disclosure, the integrated gas sensor device 10 is advantageously realized by means of an integration process flow which is compatible with the currently used manufacturing processing for realizing integrated devices.

It should be noted that the process steps being described hereinafter do not form a complete manufacturing process of integrated circuits. The present disclosure can be carried out along with the manufacturing techniques of integrated circuit being usually employed in the field, and only those steps being necessary to comprise the present disclosure have been described.

Moreover, figures showing schematic views of integrated structures during the manufacturing are not drawn in scale, being on the contrary drafted so as to emphasize the important features of the disclosure.

The integrated gas sensor device 10 comprises a substrate 11, said substrate 11 being covered by an oxide layer 13, the oxide layer 13 being thus provided on a first or top face of the substrate 11.

In particular, according to an embodiment of the disclosure, a further oxide layer 12 is provided, covering a second and opposite face of the substrate 11, in particular a bottom face of the substrate 11.

The substrate 11 may be a silicon (Si) substrate and the oxide layers 12 and 13 may be silicon oxide ($SiO_2$) layers.

More in particular, considering the coordinate system of FIG. 1, the substrate 11 is placed on the further oxide layer 12 and the oxide layer 13 is placed on the substrate 11, meaning that the first substrate 11 is sandwiched between the oxide layer 13 and the further oxide layer 12.

According to an embodiment of the disclosure, the oxide layer 13 may have a thickness between 1 and 3 µm, preferably equal to 1 µm. Moreover, the substrate 11 may have a thickness of 500 µm and the first oxide layer 12 may have a thickness between 1 and 3 µm, preferably equal to 1 µm.

The integrated gas sensor device 10 also comprises a working electrode WE, a counter electrode CE and a reference electrode RE, realized on the oxide layer 13.

Suitably, the electrodes WE, CE and RE are formed by at least a first metal and a second metal, superimposed each other. In particular, in an embodiment of the disclosure, the first metal is Titanium (Ti) and is covered by the second metal which is Platinum (Pt).

In particular, the first metal is a Titanium layer having a thickness between 5 and 30 nm, preferably equal to 20 nm and the second metal is a Platinum layer having a thickness between 80 and 120 nm, preferably equal to 100 nm.

A main opening 14 is provided in the substrate 11 reaching the oxide layer 13 and a plurality of first openings 15 and a plurality of second openings 16 are provided in the oxide layer 13 in correspondence of the working electrode WE and of the counter electrode CE, respectively. The main opening 14 is also provided in the further oxide layer 12, if any. The first and second openings 15 and 16 are through holes starting from the main opening 14 and reaching the working electrode WE and counter electrode CE, in particular the first metal of these electrodes.

Respective portions 11A, 11B of the substrate 11 are disposed on opposite sides of the main opening 14. Moreover, respective portions 12A, 12B of the further oxide layer 12, if any, are also disposed on opposite sides of the main opening 14 covering the respective portions 11A, 11B of the substrate 11. According to an embodiment of the disclosure, the main opening 14 is tapered and has a transversal dimension or a diameter which decreases starting from the substrate 11, till the oxide layer 13.

Figure 2:
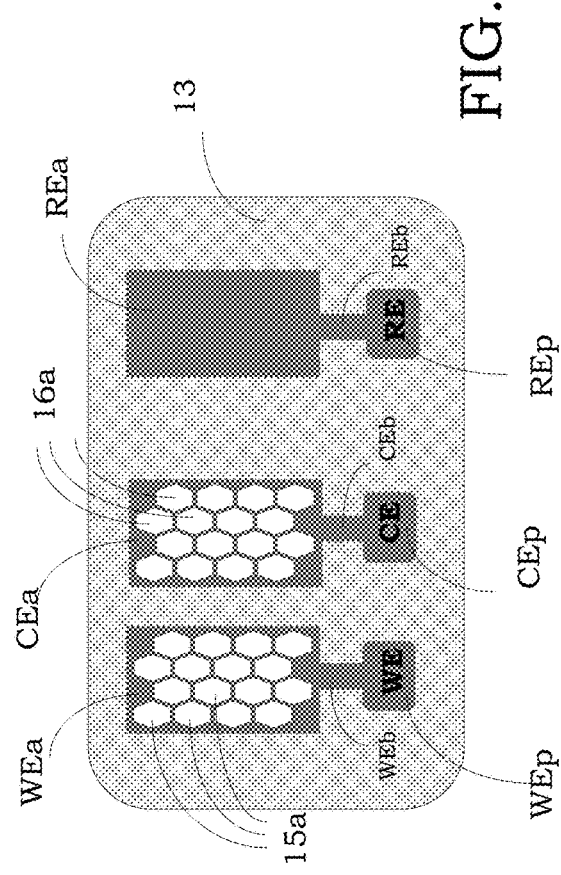
FIG. 2 schematically shows a simplified to view of the integrated gas sensor device of FIG. 1.

As shown in FIG. 2, which is a cross sectional top view of the integrated gas sensor device 10 showing a plane at the electrodes level, each electrode comprises an active area and a pad area, in electrical contact with each other by means of a conductive bridge. More in particular, the working electrode WE has an active area WEa and a pad area WEp, electrically connected to each other by a conductive bridge WEb, the counter electrode CE has an active area CEa and a pad area CEp, electrically connected to each other by a conductive bridge CEb and the reference electrode RE has an active area REa and a pad area REp, electrically connected to each other by a conductive bridge REb.

Moreover, the active area WEa of the working electrode WE comprises a plurality of third openings 15a so that the active area WEa has a grid shape. Similarly, the active area CEa of the counter electrode CE comprises a plurality of fourth openings 16a so that the active area CEa has a grid shape. According to an embodiment of the disclosure, the active areas WEa and CEa of the working and counter electrodes WE and CE, respectively, have an hexagonal grid shape.

The first openings 15 and the third openings 15a may have the same size and shape and are positioned in an aligned way, so that each of the first openings 15 in the oxide layer 13 follows a corresponding opening of the third openings 15a. Alternatively, the first openings 15 may have a smaller size and shape than the third openings 15a on the basis of the etching options of the oxide layer 13.

Similarly, the second openings 16 and the fourth openings 16a may have the same size and shape and are positioned in an aligned way, so that each of the second openings 16 in the oxide layer 13 follows a corresponding opening of the fourth openings 16a. The second openings 16 may alternative have a smaller size and shape than the fourth openings 16a, still on the basis of the etching options of the oxide layer 13.

According to an embodiment of the disclosure, these openings 15, 15a and 16, 16a have hexagonal shapes.

The integrated gas sensor device 10 also comprises an electrolyte layer portion 17A obtained by an electrolyte layer 17 and covering the working electrode WE, the counter electrode CE and the reference electrode RE.

The electrolyte layer 17 also fills in the third openings 15a of the working electrode WE and the fourth openings 16a of the counter electrode CE, but does not reach the corresponding first openings 15 and second openings 16 in the oxide layer 13.

In this way, the working electrode WE and the counter electrode CE are in contact with the environmental air through the main opening 14, the first openings 15 and the third openings 16, respectively, while the reference electrode RE is isolated from the environmental air due to the presence of the portion 11A of the substrate 11. In particular, the electrolyte layer 17 that fills in the fourth and fifth openings 15a and 16a of the working and counter electrodes WE and CE, respectively, realizes the corresponding active areas WEa and CEa being in contact with the environmental air.

In particular, the electrolyte layer portion 17A has a promoted adhesion on the oxide layer 13.

The electrolyte layer can be made of any suitable material capable of providing the electrolytic system for the sensing and counter reactions and adapted to realize a suitable interface to the electrodes.

It should be remarked that additional advantages are obtained when the electrolyte layer 17 is:
a good protonic conductor;
a good solvent for reactants and products of the electrochemical reaction of the sensed gas; and
chemically and physically stable for fabrication and operation of sensors.

For instance, the electrolyte layer 17 may comprise an aqueous system of acids, bases and salts or a polymer electrolyte. Alternatively, the electrolyte layer 17 may comprise a non aqueous system like propylene carbonate, lithium perchlorate, polyethylene oxide lithium chloride, ionic liquid.

According to a preferred embodiment of the disclosure, for an optimal CO sensing, the electrolyte layer 17 may be Nafion®, produced by DuPont, which is a sulfonated tetrafluoroethylene based fluoropolymer-copolymer and has a suitable ionic conductibility due to H+ hoping through $SO_{3-}$ groups. Moreover, Nafion® is available as a solid membrane or as a liquid solution to be dispensed, having good wetting properties tested on a silicon (Si) oxide and on polyethylene naphthalate (PEN) substrates.

The integrated gas sensor device 10 also comprises a hydrogel layer portion 18A obtained from a hydrogel layer 18 and placed on the electrolyte layer portion 17A. The electrolyte layer portion 17A and the hydrogel layer portion 18A have some dimensions that are the same size, such as perimeter dimensions, suitable to cover at least the working electrode WE, the counter electrode CE and the reference electrode RE. In this way, the hydrogel layer portion 18A acts as a "quasi solid state" water reservoir for the integrated gas sensor device 10. It is to be appreciated, however, that the electrolyte layer portion 17A and the hydrogel layer portion 18A may have the same or different thicknesses.

In particular, for an optimal CO sensing, the hydrogel can be chosen between the electrolytic hydrogels, such as 2-Hydroxyethylmethacrylate (HEMA) and ethylene glycol dimethacrylate (EGDM), polyvinyl alcohol (PVA), polyethylene glycol diacrylate (PEG-DA). In this case, the electrolytic hydrogel combines the functionalities of both electrolyte and hydrogel layers in a single layer.

Finally, the integrated gas sensor device 10 comprises a capping layer 19, covering the electrolyte layer portion 17A and the hydrogel layer portion 18A and being in contact with both the same and the second oxide layer 13. The capping layer 19 is thus shaped as an inverse U or another shape suitable to obtain a closed volume containing the electrolyte layer portion 17A and the hydrogel layer portion 18A.

According to an embodiment of the disclosure, the capping layer 19 can be made of polymide, polyesther, polyurethane, polytetrafluoroethylene, and any other non reactive thermoplastic materials and can have a thickness between 50 and 400 µm, preferably equal to 100 µm.

The integrated gas sensor device 10 is obtained by a process flow which is adapted to be carried out according to the current manufacturing processes and technologies for integrating electronic devices, said process flow comprising the following process steps (also depicted in FIGS. 3A-3I).

Figure 3A:
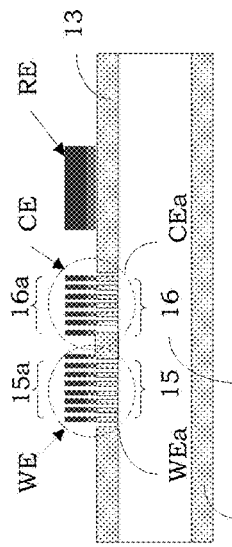

As depicted in FIG. 3A, an oxide layer 13 is deposited on a substrate 11, the oxide layer 13 being thus provided on a first or top face of the substrate 11. In particular silicon oxide ($SiO_2$) layer is provided on a silicon (Si) substrate.

A further oxide substrate 12 may be provided covering a second and opposite face of the substrate 11, in particular a bottom face of the substrate 11. In particular, also the further oxide layer 12 may be a silicon oxide ($SiO_2$) layer.

Figure 3B:
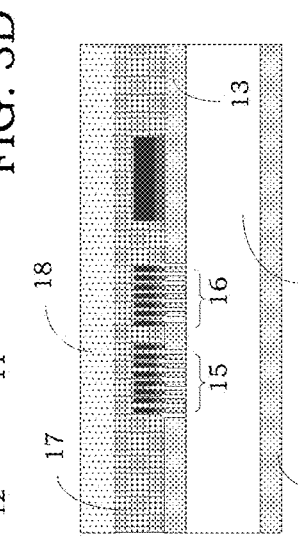

A deposition of a first metal layer 20 on the oxide layer 13 and of a second metal layer 21 on the first metal layer 20 is carried out, as depicted in FIG. 3B. It should be remarked that such a single deposition step allows to deposit the working, counter and reference electrodes, WE, CE and RE, at once.

According to an embodiment of the disclosure, this step of deposition comprises depositing a first metal layer 20 of Titanium (Ti) having a thickness between 5 and 30 nm, preferably equal to 20 nm and a second metal layer 21 of Platinum (Pt) having a thickness between 80 and 120 nm, preferably equal to 100 nm.

Figure 3C:
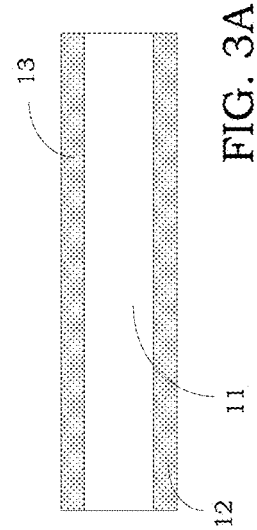

As depicted in FIG. 3C, the process comprises a patterning step of the metal layers 20 and 21. In particular, such patterning step defines the reference electrode RE as well as the working electrode WE and the counter electrode CE, all being realized simultaneously.

Moreover, according to this patterning step, also the third and fourth openings 15a and 16a of the working electrode WE and of the counter electrode CE, respectively, are patterned. According to an embodiment of the disclosure, said third and fourth openings 15a and 16a are patterned so as to have an hexagonal shape.

Figure 3D:
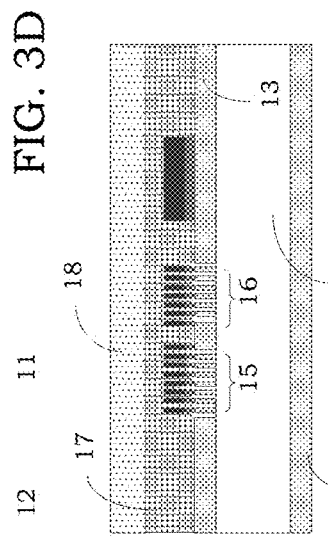

The process comprises an etching step of the oxide layer 13, as depicted in FIG. 3D, that can be done in different ways, in particular according to different etching options of this oxide layer 13. The etching step of the oxide layer 13 can be further optimized or engineered by a skilled person in order to obtain the envisaged device structure.

This etching step in particular opens the first and second openings 15 and 16 in the oxide layer 13, in particular in correspondence with the third and fourth openings 15a and 16a, respectively, as depicted in FIG. 3D. According to an embodiment of the disclosure, this etching step of the oxide layer 13 is a dry etching step.

More in particular, since the first and second openings 15 and 16 are realized by an etching step following the patterning step of the third and fourth openings 15a and 16a, the first and second openings 15 and 16 may have the same size and shape than the third and fourth openings 15a and 16a, respectively. Alternatively, the first and second openings 15 and 16 may have a smaller size and shape than the third and fourth openings 15a and 16a, respectively.

In this way, the oxide layer 13 is substantially a membrane like layer, which comprises the first and second openings 15 and 16 as pores. According to an embodiment of the disclosure, these pores have a diagonal from about 2 to about 15 µm and a pitch of 26 µm, being deep as the oxide layer 13, for instance 1 µm or more.

Hence, the active areas WEa and CEa of the working and counter electrodes WE and CE, respectively, are defined, in particular with a grid like shape.

More particularly, the etching step may comprise a photolithographic process which uses a lithography mask for defining further openings, 15 and 16, in the oxide layer 13, in correspondence with the openings, 15a and 16a, of the working and counter electrodes, WE and CE, the further openings 15 and 16 in the oxide layer 13 having a smaller size and shape than the openings 15a and 16a of the working and counter electrodes, WE and CE.

Alternatively, the etching step may use the first and second metal layers, 20 and 21, already patterned, as a hard mask combined with a further mask in order to define respective further openings 15 and 16 in the oxide layer 13, in correspondence with the openings 15a and 16a of the working and counter electrodes, WE and CE. In this case, the further openings 15 and 16 in the oxide layer 13 have the same size and shape than the openings 15a and 16a of the working and counter electrodes WE and CE.

Figure 3E:
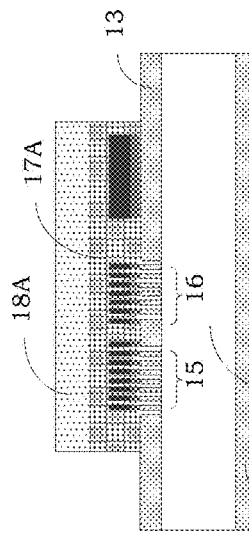

As depicted in FIG. 3E, the process comprises a deposition step of an electrolyte layer 17 on the oxide layer 13 and a deposition step of a hydrogel layer 18 on the electrolyte layer 17.

A step of surface treatment with alkane silanes, such as APTES (3-Aminopropyl triethoxysilane), of the oxide layer 13 may be realized before the deposition of the electrolyte layer 17 so as to obtain a promoted adhesion the electrolyte layer 17 on the oxide layer 13.

According to an embodiment of the disclosure, the deposition step of the electrolyte layer 17 comprises a spin coating step of an electrolyte, which may be followed by an annealing step at a temperature of 140° C. and by a socking step in sulfuric acid ($H_2SO_4$) at a temperature of 90° C. and with a concentration of 0.5M.

According to an embodiment of the disclosure, the deposition step deposits an electrolyte layer 17 being chosen between an aqueous system of acids, bases and salts, a polymer electrolyte, a non aqueous system like propylene carbonate, lithium perchlorate, polyethylene oxide lithium chloride, ionic liquids.

According to a preferred embodiment of the disclosure, for an optimal CO sensing, the spin coating step deposits an electrolyte layer 17 of Nafion®, which is a sulfonated tetrafluoroethylene based fluoropolymer-copolymer produced by DuPont.

In particular, the deposition step of the electrolyte layer 17 fills in the third openings 15a of the working electrode WE and the fourth openings 16a of the counter electrode CE, thus completing the active areas WEa and CEa of the working and counter electrodes WE and CE, respectively.

The deposition step of the hydrogel layer 18 also comprises a spin coating step of the hydrogel layer 18.

Figure 3F:
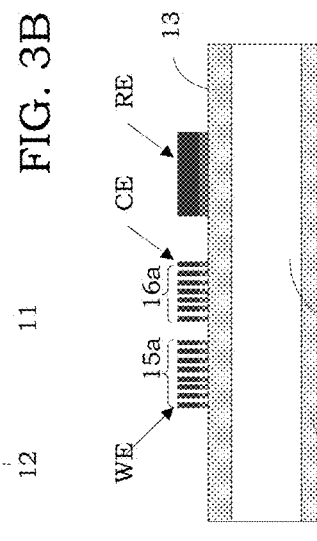

The process comprises a step of etching the electrolyte layer 17 and the hydrogel layer 18, in order to obtain the electrolyte layer portion 17A and the hydrogel layer portion 18A, as depicted in FIG. 3F. According to an embodiment of the disclosure, this etching step of the electrolyte layer 17 and of the hydrogel layer 18 is a dry etching step.

The process may also comprise a subsequent step of soaking in water ($H_2O$) at a temperature of 90° C.

According to an embodiment of the disclosure, the spin coating step deposits a wetting layer as hydrogel layer 18, which acts as a "quasi solid state" water reservoir able to overcome the limits of solid and liquid electrolytes.

In particular, for an optimal CO sensing, the spin coating step deposits a hydrogel layer 18 being chosen between the electrolytic hydrogels, such as 2-Hydroxyethylmethacrylate (HEMA) and ethylene glycol dimethacrylate (EGDM), polyvinyl alcohol (PVA), polyethylene glycol diacrylate (PEG-DA).

The process comprises a further deposition step of the capping layer 19, covering the electrolyte layer portion 17A and the hydrogel layer portion 18A and contacting the oxide layer 13 which has been left free after the step of dry etching the electrolyte layer 17 and the hydrogel layer 18 at the opposite sides of the electrolyte layer portion 17A, as depicted in FIG. 3G.

At this point, the process comprises a step of exposing the active areas WEa and CEa of the working and counter electrodes WE and CE to an environmental air.

In particular, according to an embodiment of the disclosure, the process comprises back cell steps, in particular using micromachining, to be performed on the substrate 11.

More in particular, the process may comprise a step of dry etching the further oxide layer 12, if any, which opens an aperture 14A and defines respective portions 12A and 12B of the further oxide layer 12, as shown in FIG. 3H.

According to this embodiment, the process comprises a step of deep back etching of the substrate 11 which is a dry etching step, in case performed through the aperture 14A, in order to define the main opening 14 through the substrate 11 till the oxide layer 13 and thus expose the first openings 15 and second openings 16, as shown in FIG. 3I, which corresponds to FIG. 1.

In particular, this step of deep back etching of the substrate 11 uses micromachining.

In this way, an integrated gas sensor device 10 is obtained, which comprises working and counter electrodes, WE and CE having a plurality of openings, 15a and 16a, as well as further openings, 15 and 16, realized in the oxide layer 13 covering the substrate 11 of the integrated gas sensor device 10, and a main opening 14 realized in the substrate 11 in correspondence of the working and counter electrodes, WE and CE in such a way that the respective active areas of these electrodes are exposed to the environmental air.

Figure 4:
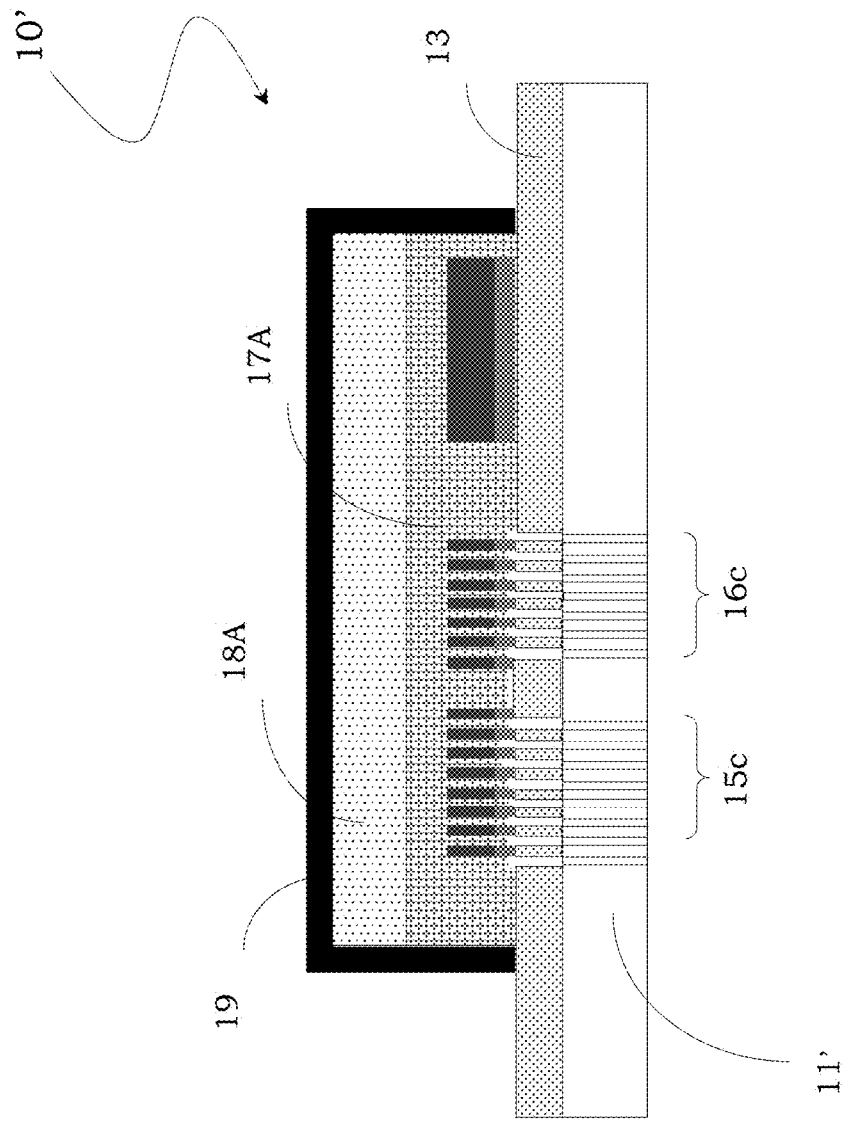
FIG. 4 schematically shows a side view of an integrated gas sensor device realized according to an alternative embodiment of the disclosure.

An alternative embodiment of the integrated gas sensor device according to the disclosure is depicted in FIG. 4, globally indicated with 10'.

To structurally and/or functionally equal elements with respect to the integrated gas sensor device described with reference to FIGS. 1, 2 and 3A-3I, same reference numbers will be applied and the detailed description thereof will be avoided for sake of simplicity.

The integrated gas sensor device 10' according to this alternative embodiment in particular comprises a plurality of trench-like openings 15c and 16c realized in a worked substrate layer as substrate 11' in correspondence with the openings realized in the working and counter electrodes, WE and CE, and namely the openings 15a and 16a, and the further openings realized in the oxide layer 13, namely the further openings 15 and 16.

It is thus evident that, also according to this alternative embodiment, the integrated gas sensor device 10' comprises working and counter electrodes, WE and CE having a plurality of openings, 15a and 16a, as well as further openings, 15 and 16, realized in the oxide layer 13 covering the substrate 11 of the integrated gas sensor device 10, and trench-like openings 15c and 16c, realized in the substrate 11' in correspondence of the working and counter electrodes, WE and CE in such a way that the respective active areas of these electrodes are exposed to the environmental air.

As previously described with reference to FIG. 1, the integrated gas sensor device 10' also comprises an electrolyte layer portion 17A obtained by an electrolyte layer 17 and covering the working electrode WE, the counter electrode CE and the reference electrode RE, as well as a hydrogel layer portion 18A obtained from a hydrogel layer 18 and placed on the electrolyte layer portion 17A, the hydrogel layer portion 18A acts as a "quasi solid state" water reservoir for the integrated gas sensor device 10'.

Moreover, a capping layer 19 may be provided, covering the electrolyte layer portion 17A and the hydrogel layer portion 18A and being shaped as an inverse U or another shape suitable to obtain a closed volume containing the electrolyte layer portion 17A and the hydrogel layer portion 18A.

The same material and size can be used for the corresponding elements and layers as the one described with reference to the previous embodiment.

Also the integrated gas sensor device 10' according to this alternative embodiment may be obtained by a process flow which is adapted to be carried out according to the current manufacturing processes and technologies for integrating electronic devices, as depicted in FIGS. 5A-5I.

Also in this case, same reference numbers will be applied to corresponding element and layers and the detailed description of the corresponding method steps will be avoided for sake of simplicity, in particular the steps depicted in FIGS. 5A to 5D, which correspond to the steps depicted in FIGS. 3A to 3D.

According to this alternative embodiment, after the step of etching the oxide layer 13 so as to open the first and second openings 15 and 16 in the oxide layer 13 in correspondence with the third and fourth openings 15a and 16a of the working and counter electrodes, WE and CE, the process comprises a step of realizing deep trenches 15b and 16b by further etching the substrate 11 in correspondence with the first and second openings 15 and 16 of the oxide layer 13.

In particular, this step of realizing the deep trenches 15b and 16b in the substrate 11 comprises a deep reactive ion etching step which uses a same lithographic mask as the one used to obtain the first and second openings 15 and 16 in the oxide layer 13 by deep etching further in the silicon substrate layer 11 until a given depth D, for instance in the range of 80 to 120 micron, as depicted in FIG. 5E.

In particular, the deep reactive ion etching step realizes deep trenches 15b and 16b having the same size and shape than the openings 15a and 16a of the working and counter electrodes WE and CE.

As depicted in FIG. 5F, the process comprises a deposition step of an electrolyte layer 17 on the oxide layer 13 and a deposition step of a hydrogel layer 18 on the electrolyte layer 17.

The process comprises a step of etching the electrolyte layer 17 and the hydrogel layer 18, in order to obtain the electrolyte layer portion 17A and the hydrogel layer portion 18A, as depicted in FIG. 5G.

The process comprises a further deposition step of the capping layer 19, covering the electrolyte layer portion 17A and the hydrogel layer portion 18A, as depicted in FIG. 5H.

At this point, the process comprises a step of exposing the active areas working and counter electrodes WE and CE to an environmental air, as depicted in FIG. 5I.

In particular, according to this embodiment of the disclosure, the process comprises a back-grinding step to remove part of the substrate 11 which is thinned down to a thinned substrate layer acting as substrate 11' for the integrated gas sensor device 10'. In particular, the back-grinding step is performed until reaching the deep trenches 15b and 16b and thus realizing the trench-like openings 15c and 16c from a back side of the substrate 11. In this way, the trench-like openings 15c and 16c and the corresponding openings 15 and 16 realized in the oxide layer 13 and the openings 15a and 16a of the working electrode WE and counter electrode CE form a path for a gas flow from the backside of the integrated gas sensor device 10' to the active areas WEa and CEa of the working electrode WE and counter electrode CE, as also shown in FIG. 4, which corresponds to FIG. 5I.

In essence, according to the embodiments of the disclosure, an integrated gas sensor device is provided, said device being miniaturized and obtained by a process flow which is compatible with the currently used manufacturing process for integrating electronic devices.

The integrated gas sensor device has a fast response, due to the presence of a gas inlet, through the first opening and the second and third openings, on the back of the device. In this way, the sensed gas, in particular carbon monoxide (CO), diffuses from environmental air to the electrodes surface.

As already underlined, the gas permeable structure comprises suitable openings in correspondence of the working electrode WE and of the counter electrode CE, but all electrodes, also the reference electrode RE, are realized by the same deposition and etching steps, at once.

Furthermore, the working electrode WE and counter electrode CE may have a grid shape, in particular an hexagonal grid shape, able to optimize electrode efficiency.

Finally, the integrated gas sensor device also comprises a hydrogel layer portion deposited on the electrolyte layer portion and acting as a "quasi solid" water reservoir.

For an optimal CO sensing, an electrolyte layer made of Nafion® is used and the hydrogel is chosen between 2-Hydroxyethylmethacrylate (HEMA) and ethylene glycol dimethacrylate (EGDM), polyvinyl alcohol (PVA), polyethylene glycol diacrylate (PEG-DA).

Obviously, a technician of the field, aiming at meeting incidental and specific desires, will bring several modifications to the above described integrated gas sensor device and corresponding manufacturing process, all within the scope of protection of the disclosure.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:
   forming a first insulating layer on a first side of a substrate, the substrate having a second side opposite the first side;
   forming a patterned layer on the first insulating layer, the patterned layer having a first electrode, a second electrode, and a third electrode, the forming the patterned layer including forming first through holes in at least one of the first electrode and the second electrode; and
   forming a electrolytic hydrogel layer on the patterned layer, first portions of the electrolytic hydrogel layer being between the first, second, and third electrodes, respectively, and second portions of the electrolytic hydrogel layer being in at least one of the first through holes.

2. The method of claim 1 wherein the electrolytic hydrogel layer includes an electrolyte layer and a hydrogel layer on the electrolyte layer.

3. The method of claim 1, further comprising:
   exposing the electrolytic hydrogel layer to the external environment by etching a through hole in the second side of the substrate.

4. The method of claim 3 wherein the exposing the electrolytic hydrogel layer includes etching the through hole through the first insulating layer to the first portions of the electrolytic hydrogel layer.

5. The method of claim 1 wherein the forming the patterned layer includes forming a first metal layer and a second metal layer on the first metal layer, the first, second and third electrodes each etched from the first and second metal layers, the first electrode being a working electrode, the second electrode being a counter electrode, and the third electrode being a reference electrode.

6. The method of claim 1, further comprising:
   forming a capping layer, the capping layer in contact with the electrolytic hydrogel layer, and the first insulating layer.

7. The method of claim 5, wherein forming the patterned layer includes the first through holes having a hexagonal shape.

8. The method of claim 1, further comprising:
   etching the first layer to form second through holes in the first insulating layer, the second through holes abutting the first through holes.

9. The method of claim 8, further comprising:
   exposing active areas of the working and counter electrodes to an external environment.

10. The method of claim 9, wherein the exposing the active areas of the working and counter electrodes to the external environment includes forming a through hole completely through the substrate between the first and second sides.

11. The method of claim 9, wherein the exposing the active areas of the working and counter electrodes to the external environment includes forming a plurality of third through holes extending completely through the substrate between the first and second sides, the third through holes being aligned with the second through holes, respectively.

12. The method of claim 8, wherein the etching the insulating layer includes using a lithography mask to form the second through holes in the first insulating layer, the second through holes being smaller than the first through holes.

13. The method of claim 8, wherein the forming the patterned layer includes forming a first metal layer and a second metal layer on the first metal layer, and the etching the insulating layer includes forming a mask to define the second through holes in the first insulating layer and using the first and second metal layers as an etch stop.

14. The method of claim 1, further comprising:
etching the electrolytic hydrogel layer to expose a first portion and a second portion of the first insulating layer, the patterned layer being positioned on a third portion of the first insulating layer between the first portion and the second portion.

15. The method of claim 13, further comprising:
forming a capping layer covering the electrolytic hydrogel layer and contacting the first and second portions of the first insulating layer.

16. A method, comprising:
forming a first insulating layer on a first side of a substrate, the substrate having a second side opposite the first side, the first insulating layer having a plurality of first through holes;
forming a patterned layer on the first insulating layer, the patterned layer having a first electrode, a second electrode, and a third electrode, the first electrode and the second electrode including a plurality of second through holes, each second through hole of the plurality of second through holes aligned with a respective one of the plurality of first through holes;
forming a electrolytic hydrogel layer on the patterned layer, portions of the electrolytic hydrogel layer between each of the first, second, and third electrodes, respectively; and
exposing active areas of the first and second electrodes to an external environment.

17. The method of claim 16, wherein the electrolytic hydrogel layer includes an electrolyte layer and a hydrogel layer on the electrolyte layer.

18. The method of claim 16, wherein exposing active areas of the first and second electrodes to the external environment includes etching a through hole completely through the substrate between the first and second sides.

19. The method of claim 16, wherein forming the electrolytic hydrogel layer further includes forming portions of the electrolytic hydrogel layer in at least one of the plurality of second through holes.

20. The method of claim 16, wherein the exposing the active areas of the first and second electrodes to the external environment includes forming a plurality of third through holes extending completely through the substrate between the first and second sides, the third through holes being aligned with the second through holes, respectively.

* * * * *